(12) United States Patent
Fujinawa et al.

(10) Patent No.: US 6,990,177 B2
(45) Date of Patent: Jan. 24, 2006

(54) X-RAY OPTICAL SYSTEM FOR SMALL ANGLE SCATTERING

(75) Inventors: Go Fujinawa, Hamura (JP); Hitoshi Okanda, Hachioji (JP)

(73) Assignee: Rigaku Corporation, Tokyo (JP)

( * ) Notice: Subject to any disclaimer, the term of this patent is extended or adjusted under 35 U.S.C. 154(b) by 33 days.

(21) Appl. No.: 10/654,350

(22) Filed: Sep. 2, 2003

(65) Prior Publication Data

US 2004/0066903 A1 Apr. 8, 2004

(30) Foreign Application Priority Data

Sep. 3, 2002 (JP) ............................. 2002-257825

(51) Int. Cl.
*G21K 1/02* (2006.01)
(52) U.S. Cl. .................... 378/149; 378/70; 378/84; 378/150
(58) Field of Classification Search ............... 378/70, 378/84, 85, 145, 147, 148, 149, 150
See application file for complete search history.

(56) References Cited

U.S. PATENT DOCUMENTS

| 6,041,099 A | 3/2000 | Gutman et al. ............ 378/85 |
| 6,226,349 B1 * | 5/2001 | Schuster et al. ........... 378/84 |
| 6,330,301 B1 | 12/2001 | Jiang ....................... 378/85 |
| 6,504,902 B2 * | 1/2003 | Iwasaki et al. ............ 378/84 |
| 6,807,251 B2 * | 10/2004 | Okanda et al. ............ 378/71 |

FOREIGN PATENT DOCUMENTS

| JP | 01-172740 A | 7/1989 |
| JP | 08-313458 A | 11/1996 |
| JP | 09-229879 A | 9/1997 |
| JP | 11-287773 | 10/1999 |
| JP | 11-287773 A | 10/1999 |

OTHER PUBLICATIONS

G. Fujinawa et al: "Parallel-Slit Analyzer Developed for the Purpose of Lowering Tails of Diffraction Profiles", Journal of Applied Crystallography, Dec. 1, 1999, Munkgaard International Booksellers & Publishers, Denmark, vol. 32, Pt. 2, pp. 1145-1151, XP009029888, ISSN: 0021-8898,—*Figure 2.
Patent Abstracts of Japan, vol. 1999, No. 08, Jun. 30, 1999 and JP 11-072595 A (Rigaku Corp.), Mar. 16, 1999—Abstract only.

(Continued)

*Primary Examiner*—David V. Bruce
*Assistant Examiner*—Courtney Thomas
(74) *Attorney, Agent, or Firm*—Frishauf, Holtz, Goodman & Chick, P.C (57) ABSTRACT

An X-ray optical system for small angle scattering has a parabolic multilayer mirror and, so that switching to other X-ray incident optical systems for X-ray analysis can be easily performed. A parabolic multilayer mirror, an optical-path selecting slit device, a small-angle selecting slit device and a Soller slit are arranged between an X-ray source and a specimen-side slit. An X-ray beam having passed through the first aperture of an aperture slit plate is interrupted by the optical-path selecting slit. An X-ray beam having passed through the second aperture of the aperture slit plate is reflected at the reflecting surface of the multilayer mirror to become a parallel beam. This parallel beam passes through an aperture of the optical-path selecting slit device. The beam width is restricted by a narrow slit of the small-angle selecting slit device.

4 Claims, 8 Drawing Sheets

OTHER PUBLICATIONS

Patent Abstracts of Japan, vol. 1997, No. 09, Sep. 30, 1997 and JP 09-119906 A (Rigaku Corp.), May 6, 1997—Abstract only.

H. Klug et al: "X-ray Diffraction Procedures for Polycrystalline and Amorphous Materials", John Wiley & Sons, New York, U.S.A., 1954, pp. 634-645—entire document.

* cited by examiner

X-RAY OPTICAL SYSTEM FOR SMALL ANGLE SCATTERING

BACKGROUND OF THE INVENTION

1. Field of the Invention

The present invention relates to an X-ray optical system for small angle scattering to prepare an X-ray beam incident on a specimen in an X-ray small angle scattering apparatus.

2. Description of the Related Art

When an X-ray beam is incident on a specimen, the X-ray scatters with an angle in a range within a small angle (a small angle region) in the vicinity of the travelling direction of the X-ray beam, this being referred to as small angle scattering. Measurement of the small angle scattering provides various pieces of information, including a grain size, a periodic structure and the like, on the specimen material. An apparatus for measuring the above-described small angle scattering is referred to as an X-ray small angle scattering apparatus, and an optical system specific thereto (an optical system for preparing an X-ray beam to be incident on a specimen) is referred to as an X-ray optical system for small angle scattering.

Figure 8:
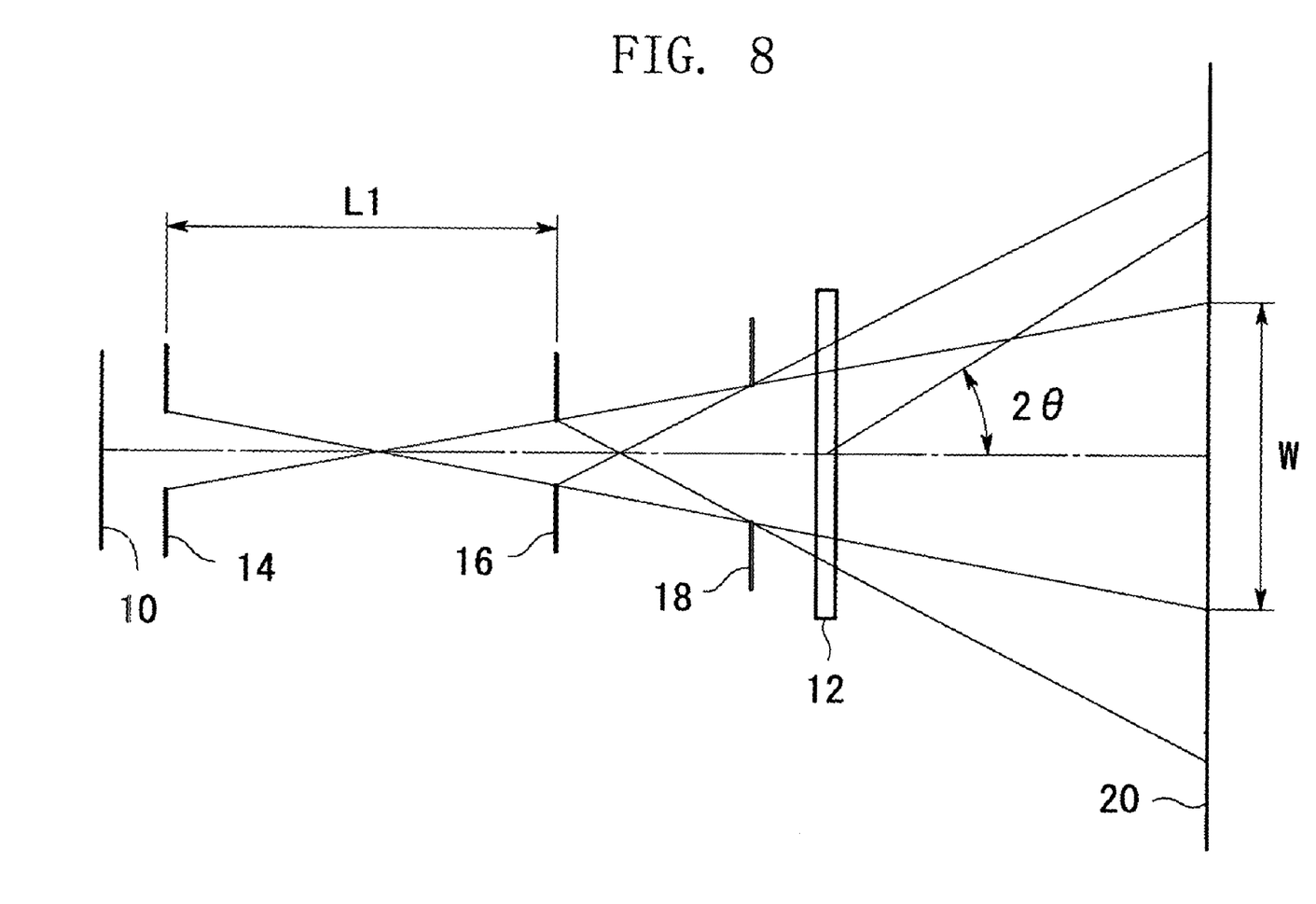
FIG. 8 is a conceptual diagram of the conventional X-ray optical system for small angle scattering.

FIG. 8 is a conceptual diagram of the conventional X-ray optical system for small angle scattering. It is noted that, in the drawing, the dimension in the direction perpendicular to the optical axis, the vertical direction in the drawing, is exaggerated. This conventional X-ray optical system for small angle scattering is referred to as a three-slit optical system. The first slit 14, the second slit 16 and the third slit 18 are arranged between an X-ray source 10 and a specimen 12 in the described order from the X-ray source side. An X-ray passing through (or reflected at) the specimen 12 is to scatter and reach an X-ray detector 20. Such a three-slit optical system is disclosed in, for example, Harold P. Klug and Leroy E. Alexander, "X-ray Diffraction Procedures for Polycrystalline and Amorphous Materials", John Wiley & Sons, 1954, p. 638.

The X-ray optical system for small angle scattering must satisfy the requirements of: a small angle of divergence (for example, 0.04 degree or less) of the X-ray beam incident on the specimen; and a small width W (for example, 0.1 mm or less) of the X-ray beam (direct beam) at a detection point. The first slit 14 and the second slit 16 serve to restrict the angle of divergence of the X-ray beam and to reduce the width of the X-ray beam (direct beam) at the detection point. The third slit 18 serves to interrupt scattered rays from the edge of the second slit 16.

Explaining actual values for realizing the above-described requirements, For example, the aperture width of the first slit 14 is set at 0.04 mm, the aperture width of the second slit 16 is set at 0.03 mm, and the distance L1 between the first slit 14 and the second slit 16 is set at 100 mm.

The above-described three-slit optical system is specific to the X-ray small angle scattering apparatus only, and accordingly a specialized X-ray small angle scattering apparatus must be prepared in order to measure the small angle scattering. Since the three-slit optical system is a special optical system, this cannot be easily switched to other X-ray incident optical systems for X-ray analysis.

SUMMARY OF THE INVENTION

Accordingly, it is an object of the present invention to provide an X-ray optical system for small angle scattering which can be easily switched to other X-ray incident optical systems for X-ray analysis. It is another object of the present invention to provide an X-ray optical system for small angle scattering which can make a monochromatic X-ray beam with an X-ray intensity larger than that of the conventional X-ray optical system for small angle scattering.

An X-ray optical system for small angle scattering according to an aspect of the present invention includes a multilayer mirror having a parabolic reflecting surface for collimating an X-ray beam, a narrow slit for restricting the width of the X-ray beam and a scattering slit in the described order from an X-ray source side. The positional relationship between the multilayer mirror and the narrow slit may be reversed. That is, the narrow slit may be arranged nearer to the X-ray source than the multilayer mirror.

An X-ray optical system for small angle scattering according to another aspect of the present invention has features described below. (a) A multilayer mirror having a parabolic reflecting surface for collimating an X-ray beam, an optical-path selecting slit device, a small-angle selecting slit device and a specimen-side slit are arranged in the described order from an X-ray source side. (b) The optical-path selecting slit device has an aperture through which the X-ray beam can pass, so that selective switching can be performed between a first state in which a parallel beam having been reflected at the multilayer mirror passes through the aperture and a second state in which the X-ray beam having bypassed the multilayer mirror passes through the aperture. (c) The small-angle selecting slit device has a narrow slit for small angle scattering measurement and a broad aperture, so that switching can be performed between a first state in which the beam width of the parallel beam having been reflected at the multilayer mirror is restricted by the narrow slit and a second state in which the parallel beam having been reflected at the multilayer mirror passes through the broad aperture. (d) The aperture center position and the aperture width of the specimen-side slit are variable. In the above-described configuration, the feature (c) may be modified in a manner that the small-angle selecting slit device may be selectively equipped with a first component having a narrow slit for small angle scattering measurement and a second component having a broad aperture.

In the present invention, the first slit of the X-ray optical system for small angle scattering of the conventional three-slit system is omitted, and the multilayer mirror is used in place thereof. Consequently, the X-ray optical system for small angle scattering can be easily switched to other X-ray incident optical systems for X-ray analysis. Furthermore, since the multilayer mirror is used, a monochromatic X-ray beam having X-ray intensity larger than that of the conventional X-ray optical system for small angle scattering can be obtained.

DESCRIPTION OF THE PREFERRED EMBODIMENTS

Figure 1:
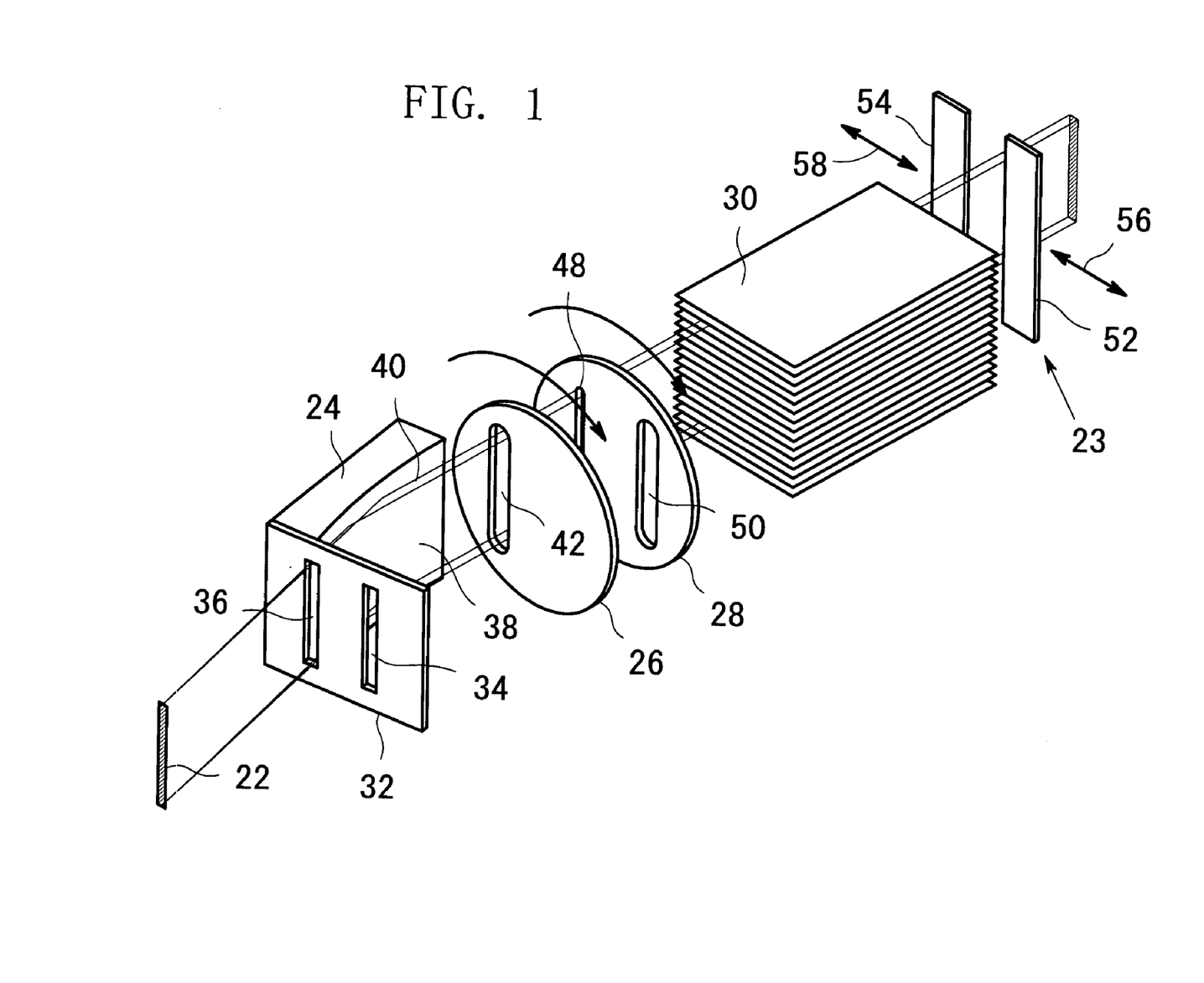
FIG. 1 is a perspective view of the first embodiment of the present invention.

Referring to FIG. 1 illustrating the first embodiment of the present invention, a multilayer mirror 24, an optical-path selecting slit device 26, a small-angle selecting slit device 28 and a Soller slit 30 are arranged between an X-ray source 22 and a specimen-side slit 23 in the described order from the X-ray source side. These constituents will be described below in detail.

An aperture slit plate 32 is fixed, with screws, on the end surface of the multilayer mirror 24 and has a first aperture 34 and a second aperture 36. An X-ray beam having passed through the first aperture 34 bypasses the multilayer mirror 24 and travels toward a specimen, this condition being to be described in detail below with reference to FIG. 5. The X-ray beam having passed through the second aperture 36 is reflected at a reflecting surface 38 of the multilayer mirror 24 to become a parallel beam 40 and travels toward the specimen. Both of the two apertures 34 and 36 have dimensions of 0.9 mm in width and about 13 mm in height.

The aperture slit plate 32 serves to prevent an unnecessary X-ray from entering into the optical system. That is, an X-ray beam 60 for the para-focusing method (see FIG. 3) and an X-ray beam 62 for both the small angle scattering measurement and the parallel beam method (see FIG. 3) can pass through the aperture slit plate 32, whereas other X-rays are prevented from entering into the incident optical system, so that the influence of the scattered X-ray is reduced.

The reflecting surface 38 of the multilayer mirror 24 has a parabolic shape, and the relative positional relationship between the multilayer mirror 24 and the X-ray source 22 is adjusted so that the X-ray source 22 is located at the focal point of the parabolic surface. Therefore, the X-ray beam reflected at the reflecting surface 38 becomes the parallel beam 40. The reflecting surface 38 is composed of a synthetic multilayer film in which heavy elements and light elements are alternately laminated and a lamination period thereof continuously varies along the parabolic line, so that an X-ray having a specific wavelength (CuKα X-ray in this embodiment) can satisfy the Bragg's law at every position on the reflecting surface 38. This type of parabolic multilayer mirror is disclosed in, for example, Japanese Patent Publication 11-287773 A (1999). The multilayer mirror 24 selectively reflects an X-ray having a specific wavelength to prepare the parallel beam 40 and, therefore, is a monochromator as well.

The parallel beam 40 obtained using the multilayer mirror 24 has an angle of divergence of 0.03 to 0.05 degree or less. Consequently, the parallel beam 40 reflected at the multilayer mirror 24 becomes parallel to have the same level of angle of divergence as that formed by the first slit and the second slit of the conventional three-slit optical system, for example, 0.04 degree. Therefore, the parallel beam 40 reflected at the multilayer mirror 24 can be used as an X-ray beam for small angle scattering measurement with the conventional first slit being omitted.

Figure 2A:
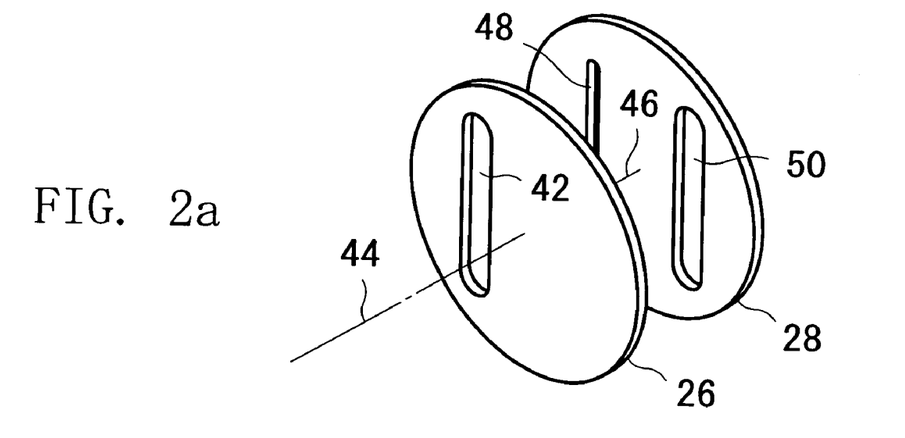
FIGS. 2a to 2c are perspective views showing three types of combination of the states of an optical-path selecting slit device and a small-angle selecting slit device.

The optical-path selecting slit device 26 is substantially in the shape of a disk and, as shown in FIG. 2a, has one slender aperture 42 at the location deviated from the center of rotation 44 of the disk. This aperture 42 has the dimensions of 3 mm in width and about 12 mm in height. The optical-path selecting slit device 26 can be turned about the center of rotation 44 through an angle of 180 degrees. In a state shown in FIG. 2a (first state), the aperture 42 is located on the left side of the center of rotation 44. When the optical-path selecting slit device 26 in the first state is turned by 180 degrees about the center of rotation 44, it becomes a state shown in FIG. 2c (second state), the aperture 42 being located on the right side of the center of rotation 44. In the state shown in FIG. 2a, only the parallel beam which has been reflected at the multilayer mirror can pass through the aperture 42. On the other hand, in the state shown in FIG. 2c, only the X-ray beam which has bypassed the multilayer mirror (the X-ray beam has a predetermined angle of divergence described below and can be used as the X-ray beam for the para-focusing method) can pass through the aperture 42.

Figure 2B:
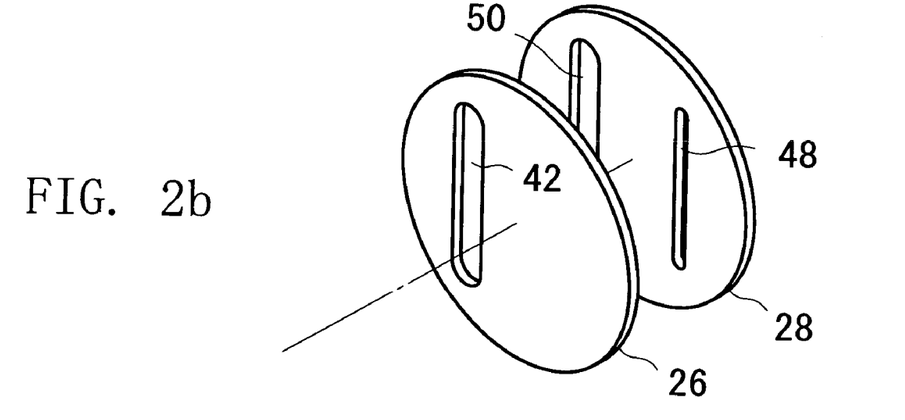
Figure 2C:
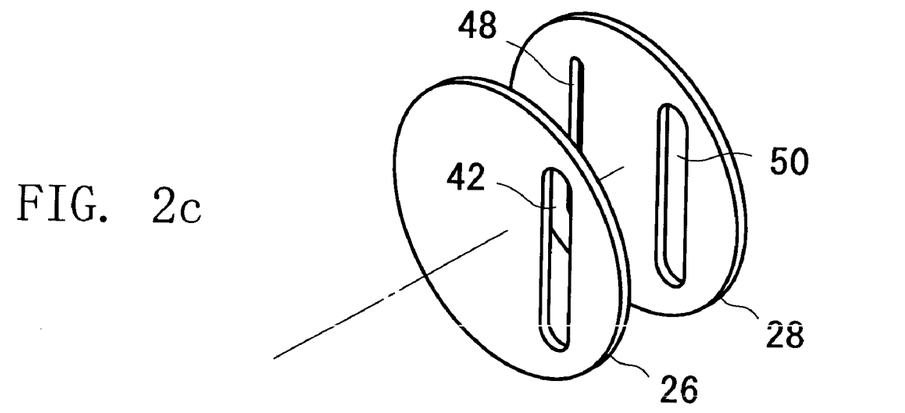

The small-angle selecting slit device 28 is substantially in the shape of a disk as well and, as shown in FIG. 2a, has a narrow slit 48 and a broad aperture 50 at diametrically opposed positions with respect to the center of rotation 46 which is in line with the center of rotation 44 of the optical-path selecting slit device 26. The narrow slit 48 serves to restrict the width of the parallel beam 40 which has been reflected at the multilayer mirror 24, and has a width of 0.03 mm and a height of about 12 mm. On the other hand, the broad aperture 50 serves to make the X-ray beam pass through, and has a width of 3 mm and a height of about 12 mm. As shown in FIG. 2a, the narrow slit 48 is located on the left side of the center of rotation 46, which is the first state, so that the beam width of the parallel beam which has been reflected at the multilayer mirror is restricted by the narrow slit 48. On the other hand, as shown in FIG. 2b, the broad aperture 50 is located on the left side of the center of rotation 46, which is the second state, so that the parallel beam which has been reflected at the multilayer mirror can pass through the broad aperture 50 as it is. This small-angle selecting slit device 28 can be modified as described below. That is, a first component having the narrow slit 48 for small angle scattering measurement and a second component having the broad aperture 50 are prepared as separate components, and these components may be selectively mounted to the small-angle selecting slit device 28, these being interchangeable with each other as necessary.

With reference to FIG. 1 again, the Soller slit 30 serves to restrict the divergence of the X-ray beam in the vertical direction. A plurality of thin blades, each having a predetermined length in the direction along the optical axis, are arranged with small spacing in the vertical direction.

The specimen-side slit 23 is composed of two slit blades 52 and 54, which can be horizontally moved independently of each other, that is, in the direction indicated by arrows 56 and 58, so that the aperture center position (the center position of the aperture in the horizontal direction) and the aperture width can be changed. Alternatively, it may be possible that two slit blades 52 and 54 are of a ganged open-close motion type and the center of the two slit blades (that is, the aperture center position) are horizontally moved by an electric motor independent of another electric motor for the ganged motion.

Figure 3:
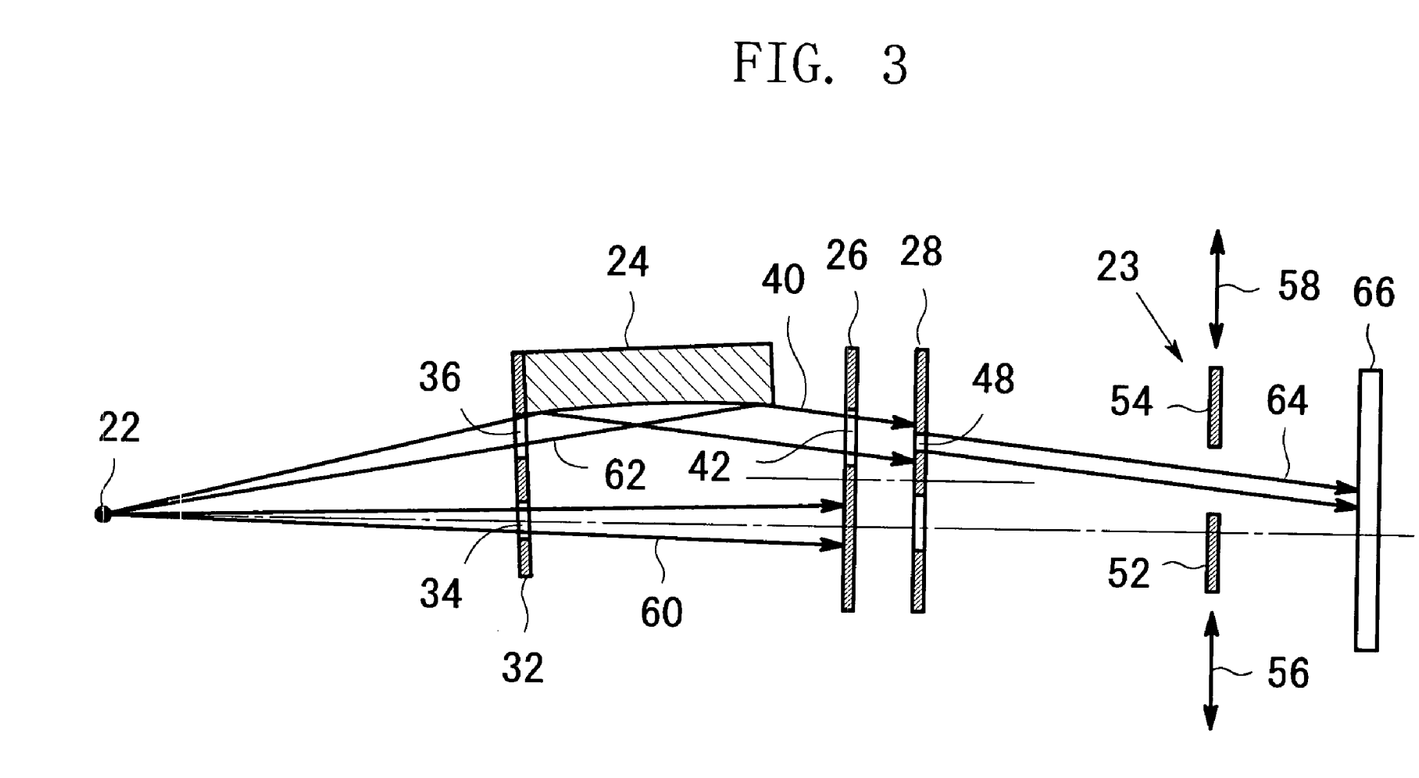
FIG. 3 is a plan view showing the setting of small angle scattering measurement.

Next, a method for using this X-ray optical system for small angle scattering will be described. FIG. 3 is a plan view of the optical system shown in FIG. 1, viewed from above. The Soller slit is not shown in the drawing. This X-ray optical system for small angle scattering can prepare three types of X-ray beam used for the small angle scattering measurement, for the measurement in the parallel beam method and for the measurement in the para-focusing method by adjusting the optical-path selecting slit device 26, the small-angle selecting slit device 28 and the specimen-side slit 23.

FIG. 3 shows a state in which the X-ray beam used for the small angle scattering measurement is obtained. The optical-path selecting slit device 26 and the small-angle selecting slit device 28 are set in the state shown in FIG. 2a. In FIG. 3, of the X-ray generated by the X-ray source 22, an X-ray beam 60 which has passed through the first aperture 34 of the aperture slit plate 32 is interrupted by the optical-path selecting slit device 26. On the other hand, an X-ray beam 62 having passed through the second aperture 36 of the aperture slit plate 32 is reflected at the reflecting surface of the multilayer mirror 24 to become the monochromatic parallel beam 40. This parallel beam 40 passes through the aperture 42 of the optical-path selecting slit device 26. Furthermore, the beam 40 passes through the narrow slit 48 of the small-angle selecting slit device 28 to become the X-ray beam 64 having a small width. Subsequently, the X-ray beam 64 passes through the specimen-side slit 23 and is incident on a specimen 66. The X-ray beam 64 has the angle of divergence which is restricted to, for example, 0.04 degree or less by the effect of the multilayer mirror 24 and the beam width which is restricted to 0.03 mm by the effect of the narrow slit 48. The scattered X-ray generated at the edge of the narrow slit 48 is interrupted by the specimen-side slit 23. The aperture center position and the aperture width of the specimen-side slit 23 can be adjusted in an optimum state by independently moving each of the slit blades 52 and 54 in the horizontal direction indicated by arrows 56 and 58. In this embodiment, each of the slits 52 and 54 are driven in the horizontal direction by an electric motor. This specimen-side slit 23 serves as a scattering slit when the X-ray beam for the small angle scattering measurement is prepared.

Comparing such an X-ray optical system for small angle scattering with the conventional three-slit optical system, the following can be said. In the conventional three-slit optical system shown in FIG. 8, the angle of divergence of the X-ray beam is restricted (collimated) by the first slit 14 and the second slit 16. In the present invention, the multilayer mirror serves for collimation. Therefore, in the present invention, the first slit in the conventional three-slit optical system is unnecessary. In the conventional three-slit optical system, a combination of the first slit 14 and the second slit 16 also serve to reduce the beam width of the X-ray beam. In the present invention, on the other hand, the narrow slit 48 serves to restrict the beam width. As a result, in the present invention, the X-ray beam for the small angle scattering measurement can be obtained with the use of a combination of the multilayer mirror 24, the narrow slit 48 and the specimen-side slit 23. If the conventional optical system is referred to as a three-slit optical system, the optical system of the present invention can be referred to as a mirror plus two-slit optical system.

Figure 4:
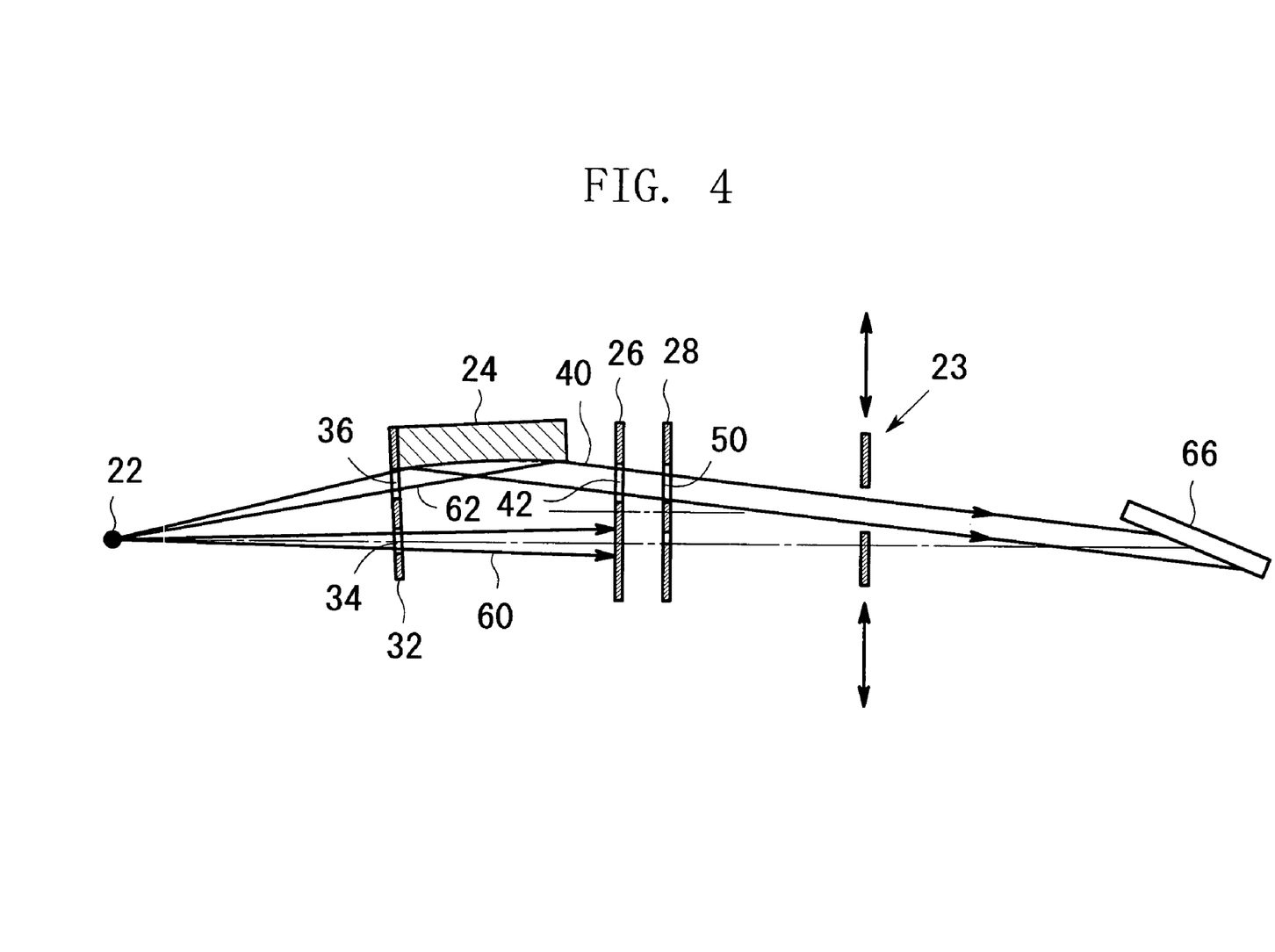
FIG. 4 is a plan view showing the setting of a parallel beam method.

Next, the setting of the parallel beam method will be described. FIG. 4 shows the setting of the parallel beam method. The optical-path selecting slit device 26 and the small-angle selecting slit device 28 are set in the state shown in FIG. 2b. In FIG. 4, of the X-ray generated by the X-ray source 22, an X-ray beam 60 having passed through the first aperture 34 of the aperture slit plate 32 is interrupted by the optical-path selecting slit device 26. On the other hand, an X-ray beam 62 having passed through the second aperture 36 of the aperture slit plate 32 is reflected at the reflecting surface of the multilayer mirror 24 to become the monochromatic parallel beam 40. This parallel beam 40 passes through the aperture 42 of the optical-path selecting slit device 26. Furthermore, the parallel beam 40 passes through also the broad aperture 50 of the small-angle selecting slit device 28 as it is. Subsequently, the parallel beam 40 passes through the specimen-side slit 23 and is incident on a specimen 66. As a result, the X-ray beam which is incident on the specimen 66 is the parallel beam 40 which has been reflected at the multilayer mirror 24. The aperture 42 of the optical-path selecting slit device 26, the broad aperture 50 of the small-angle selecting slit device 28 and the specimen-side slit 23 all impose no restriction on the parallel beam 40. When the beam width of the parallel beam 40 must be reduced to a predetermined value, it would be enough that the aperture width of the specimen-side slit 23 may be set at the desired value.

Figure 5:
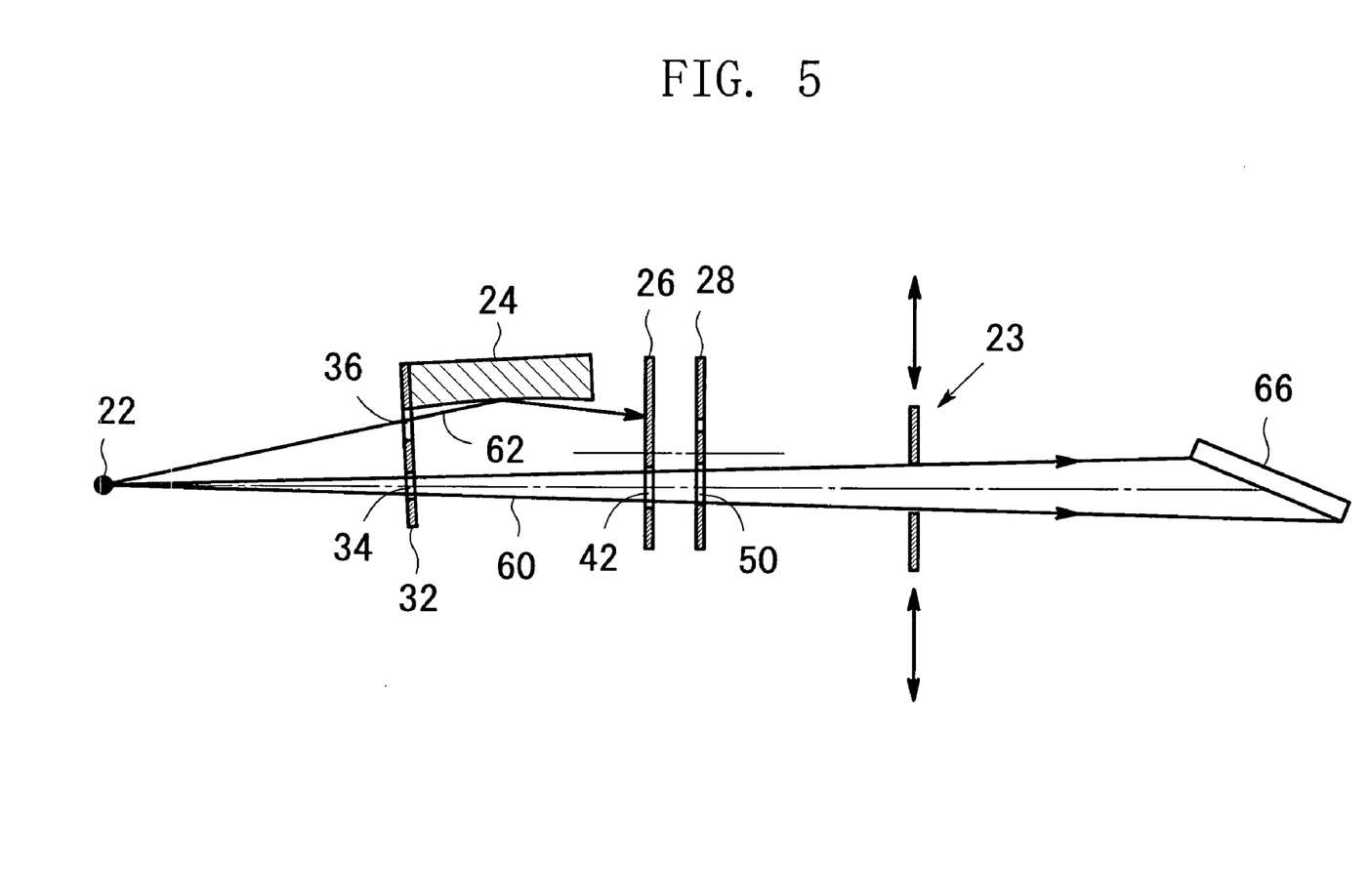
FIG. 5 is a plan view showing the setting of a para-focusing method.

Next, the setting of the para-focusing method will be described. FIG. 5 shows the setting of the para-focusing method. The optical-path selecting slit device 26 and the small-angle selecting slit device 28 are set in the state shown in FIG. 2c. In FIG. 5, of the X-ray generated by the X-ray source 22, an X-ray beam 62 having passed through the second aperture 36 of the aperture slit plate 32 is reflected at the reflecting surface of the multilayer mirror 24 to become the parallel beam 40. The beam 40 is, however, interrupted by the optical-path selecting slit device 26. On the other hand, an X-ray beam 60 having passed through the first aperture 34 of the aperture slit plate 32 passes through the aperture 42 of the optical-path selecting slit device 26. Furthermore, this divergent beam 60 passes through also the broad aperture 50 of the small-angle selecting slit device 28 as it is. Subsequently, the divergent beam 60 is restricted to have a desired angle of divergence by the specimen-side slit 23 and is incident on a specimen 66. In this case, the specimen-side slit 23 serves as a divergence slit. It is noted that the aperture center position of the specimen-side slit 23 is shifted from the state shown in FIGS. 3 and 4 and the aperture width is adjusted so that a predetermined angle of divergence is obtained.

As described above, in the X-ray optical system for small angle scattering of the present invention, the first slit, which is specific to the small angle scattering measurement, of the conventional three-slit optical system can be omitted, and the multilayer mirror, which is usable for purposes other than the small angle scattering measurement, can be used in place of the first slit. Consequently, the switching from the small angle scattering optical system to the optical system of the parallel beam method or the para-focusing method can be easily performed.

Figure 6:
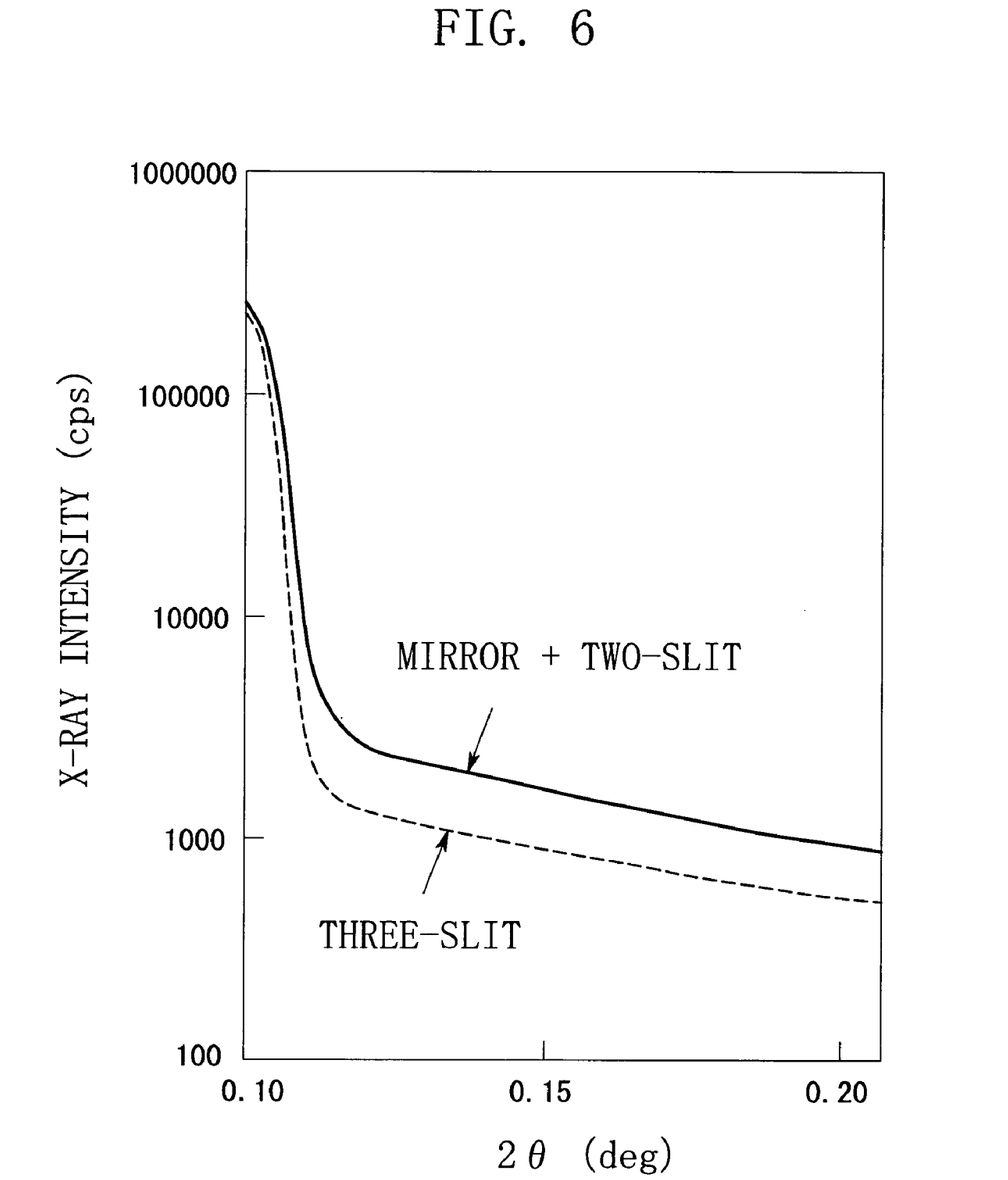
FIG. 6 is a graph showing the angle dependence of the X-ray intensity with respect to an X-ray beam for small angle scattering measurement.

FIG. 6 is a graph showing the angle dependence of the X-ray intensity with respect to an X-ray beam for small angle scattering measurement. The horizontal axis indicates a diffraction angle 2θ and the vertical axis (logarithmic scale) indicates the X-ray intensity detected with an X-ray detector (the number of counts per second in a scintillation counter). A slender slit having an aperture width of 0.1 mm is arranged in front of the X-ray detector, this slit is made to scan in the horizontal direction and, thereby, the position of the diffraction angle 2θ is changed. The graph of "three-slit" is obtained by the measurement of the X-ray beam prepared by the conventional X-ray optical system for small angle scattering shown in FIG. 8 as a direct beam, that is, no specimen is arranged. The graph of "mirror+two-slit" is obtained by the measurement of the direct beam of the X-ray beam 64 prepared by the setting for the small angle scattering measurement shown in FIG. 3. In each graph, the X-ray intensity shows a sharp decrease as the diffraction angle 2θ exceeds 0.10 degree, and substantially no influence of the direct beam is shown in the range where 2θ is 0.12 degree or more. Therefore, with respect to both the optical systems, the measurement of the scattered ray from the specimen (small angle scattering measurement) can be performed under no influence of the direct beam in the range where 2θ is 0.12 degree or more.

Figure 7:
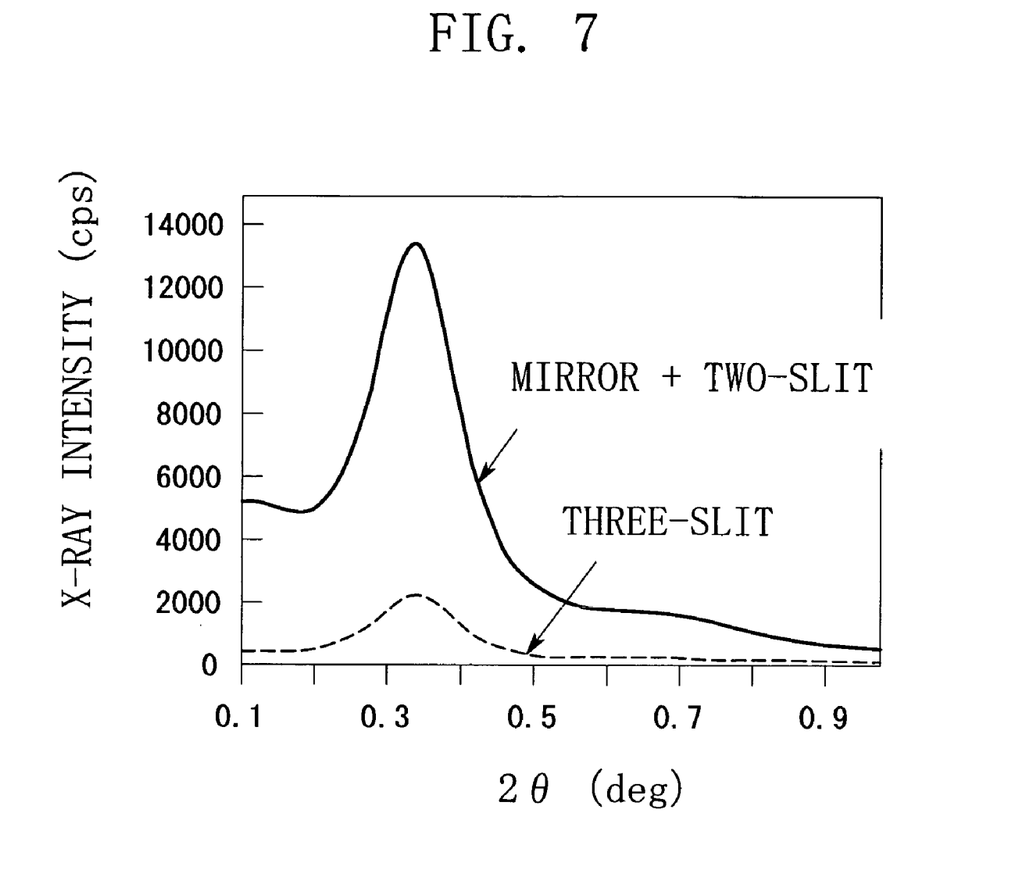
FIG. 7 is a graph showing the results of the small angle scattering measurement.

FIG. 7 is a graph showing the results of an actual measurement of the small angle scattering. The graph of "mirror+two-slit" is obtained by the measurement of the small angle scattering while the setting is in the state of the small angle scattering measurement shown in FIG. 3 and a PET (polyethylene terephthalate) sheet is used as the specimen. The graph of "three-slit" is obtained by the measurement of the small angle scattering with the conventional optical system shown in FIG. 8 for the same specimen. In the graph of "mirror+two-slit", a clear peak is observed and, in addition, a secondary peak is also observed although its peak is low. The measurement result is thus excellent because the X-ray beam prepared by "mirror+two-slit" has an intensity larger than that of the three-slit system (the intensity is 5 times or more than that of the three-slit system) and, in addition, the X-ray beam is made monochromatic.

The conditions of the measurement with respect to the graph shown in FIG. 7 will be briefly described. In FIG. 3, the distance from the X-ray source 22 to the specimen 66 is 100 mm, and the distance from the specimen 66 to the X-ray detector (scintillation counter) is 300 mm. A slender slit having an aperture width of 0.1 mm is arranged in front of the X-ray detector. This slit is made to scan in the horizontal direction, so that the position of the diffraction angle 2θ is changed.

Next, the second embodiment of the present invention will be described. In the second embodiment, referring to FIG. 1, the small-angle selecting slit device 28 may be arranged between the X-ray source 22 and the multilayer mirror 24. Even under such a configuration, the X-ray optical system for small angle scattering can be prepared in a manner similar to that in the optical system shown in FIG. 1 and, in addition, this optical system can be easily switched to the optical system for the parallel beam method and the para-focusing method.

The third embodiment of the present invention will be described. In the third embodiment, the small-angle selecting slit device 28 may be removed, and a scattering slit is arranged between the specimen-side slit 23 and the specimen in the optical system shown in FIG. 1. When the small angle scattering measurement is performed, the aperture width of the specimen-side slit 23 is reduced so as to serve as a narrow slit.

The fourth embodiment of the present invention will be described. In the fourth embodiment, the conventional three-slit optical system shown in FIG. 8 may be used provided that the first slit 14 is replaced by a multilayer mirror. In this case, switching to the optical systems for the parallel beam method and the para-focusing method is impossible. However, as indicated in the graph shown in FIG. 7, an improvement in measurement precision is expected because of the performance of the multilayer mirror.

What is claimed is:

1. An X-ray optical system for small angle scattering, comprising:
   a multilayer mirror having a parabolic reflecting surface for collimating an X-ray beam,
   a narrow slit for restricting a width of the X-ray beam, and
   a scattering slit in described order from an X-ray source sides, said scattering slit having an aperture center whose position is variable and an aperture width which is variable.

2. An X-ray optical system for small angle scattering, comprising:
   a narrow slit for restricting a width of an X-ray beam,
   a multilayer mirror having a parabolic reflecting surface for collimating the X-ray beam, and
   a scattering slit in described order from an X-ray source side, said scattering slit having an aperture center whose position is variable and an aperture width which is variable.

3. An X-ray optical system for small angle scattering, in which:
   (a) a multilayer mirror having a parabolic reflecting surface for collimating an X-ray beam, an optical-path selecting slit device, a small-angle selecting slit device and a specimen-side slit are arranged in the described order from an X-ray source side;
   (b) the optical-path selecting slit device has an aperture through which the X-ray beam can pass, so that selective switching can be performed between a first state in which a parallel beam having been reflected at the multilayer mirror passes through the aperture and a second state in which an X-ray beam having bypassed the multilayer mirror passes through the aperture;
   (c) the small-angle selecting slit device has a narrow slit for small angle scattering measurement and a broad aperture, so that switching can be performed between a first state in which a beam width of the parallel beam having been reflected at the multilayer mirror is restricted, by the narrow slit and a second state in which the parallel beam having been reflected at the multilayer mirror passes through the broad aperture; and
   (d) an aperture center position and an aperture width of the specimen-side slit are variable.

4. An X-ray optical system for small angle scattering, in which:
   (a) a multilayer mirror having a parabolic reflecting surface for collimating an X-ray beam, an optical-path selecting slit device, a small-angle selecting slit device and a specimen-side slit are arranged in the described order from an X-ray source side;
   (b) the optical-path selecting slit device has an aperture through which the X-ray beam can pass, so that selective switching can be performed between a first state in which a parallel beam having been reflected at the multilayer mirror passes through the aperture and a second state in which an X-ray beam having bypassed the multilayer mirror passes through the aperture;
   (c) the small-angle selecting slit device can be selectively equipped with a first component having a narrow slit for small angle scattering measurement and a second component having a broad aperture; and
   (d) the specimen-side slit has an aperture for small angle scattering measurement, and its aperture center position and its aperture width are variable.

* * * * *